US007541422B2

(12) United States Patent
DiCosimo et al.

(10) Patent No.: US 7,541,422 B2
(45) Date of Patent: Jun. 2, 2009

(54) ENZYME-CATALYZED PROCESS FOR THE PREPARATION OF MACROCYCLIC POLYESTER OLIGOMERS

(75) Inventors: Robert DiCosimo, Chadds Ford, PA (US); Scott Christopher Jackson, Wilmington, DE (US); Anna Panova, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 386 days.

(21) Appl. No.: 11/444,631

(22) Filed: Jun. 1, 2006

(65) Prior Publication Data

US 2007/0021584 A1      Jan. 25, 2007

Related U.S. Application Data

(60) Provisional application No. 60/688,220, filed on Jun. 7, 2005.

(51) Int. Cl.
*C08G 63/02*       (2006.01)
*C08G 64/00*       (2006.01)

(52) U.S. Cl. .................. 528/272; 424/451; 424/456; 435/18; 435/134; 435/136; 524/589; 524/732; 524/768; 528/271; 528/274

(58) Field of Classification Search .............. 524/732, 524/768, 589; 528/274, 271, 272; 424/451, 424/456; 435/18, 134, 136
See application file for complete search history.

(56) References Cited

U.S. PATENT DOCUMENTS

| 5,231,161 | A | 7/1993 | Brunelle et al. |
| 5,407,984 | A | 4/1995 | Brunelle et al. |
| 5,466,744 | A | 11/1995 | Evans et al. |
| 5,661,214 | A | 8/1997 | Brunelle et al. |
| 5,668,186 | A | 9/1997 | Brunelle et al. |
| 6,787,632 | B2 * | 9/2004 | Phelps et al. ............... 528/480 |
| 6,979,720 | B2 * | 12/2005 | Brugel et al. ............... 528/274 |
| 2004/0019177 | A1 | 1/2004 | Brugel et al. |
| 2005/0054809 | A1 | 3/2005 | Brugel et al. |

FOREIGN PATENT DOCUMENTS

| EP | 098 367 A2 | 3/2000 |
| WO | WO03/093491 A1 | 11/2003 |

OTHER PUBLICATIONS

Lipase-catalyzed Synthesis of Aromatic Polyesters, Journal of Industrial Microbiology & Biotechnology (1998).

* cited by examiner

*Primary Examiner*—Terressa M Boykin

(57) ABSTRACT

A process for the enzyme-catalyzed preparation of cyclic ester oligomers from dicarboxylic acids and/or dicarboxylic acid derivatives and diols, hydroxycarboxylic acids and/or hydroxycarboxylic acid esters, and/or linear ester oligomers in the presence of a solvent comprising a tertiary alcohol and a non-alcoholic solvent.

24 Claims, No Drawings

ENZYME-CATALYZED PROCESS FOR THE PREPARATION OF MACROCYCLIC POLYESTER OLIGOMERS

FIELD OF THE INVENTION

The present invention relates to a process for the enzyme-catalyzed preparation of cyclic ester oligomers from dicarboxylic acids and/or dicarboxylic acid derivatives and diols, hydroxycarboxylic acids and/or hydroxycarboxylic acid esters, and/or linear ester oligomers using a reaction solvent mixture comprising a tertiary alcohol and non-alcoholic solvent.

BACKGROUND OF THE INVENTION

Cyclic ester oligomers (CEOs) have been known for a long time; see for instance U.S. Pat. No. 2,020,298. They are known to be present in varying, usually small, quantities in many linear polyesters and have been isolated from such linear polyesters; see for example A. G. Harrison, "Analysis of cyclic oligomers of poly(ethylene terephthalate) by liquid chromatography/mass spectrometry", *Polymer*, 38(10), 2549-2555 (1997) and G. Wick, H. Zeitler, "Cyclic Oligomers in polyesters from diols and aromatic dicarboxylic acids", *Angewandte Makromolekulare Chemie*, (1983), 112, 59-94. They are often low viscosity liquids, and it has been known for a long time that they may be polymerized to higher molecular weight linear polyesters by ring opening polymerization; see for instance U.S. Pat. Nos. 5,466,744 and 5,661,214 and references cited therein. This ability to readily form a high molecular weight polymer from a relatively low viscosity liquid has made CEOs attractive as materials for manufacturing processes wherein a low viscosity material is converted to a high molecular polymer in a mold, so that a final shaped part is obtained. They are also attractive candidates as coatings and as encapsulants for electrical components and electronic devices.

However such CEOs have been difficult and expensive to prepare, for example requiring very high dilution conditions and/or using relatively expensive starting materials such as diacyl halides in conjunction with diols and a base to react with the HCl formed; see for instance U.S. Pat. No. 5,466,744. These high manufacturing costs have in many cases prevented the use of CEOs commercially, and therefore lower cost routes to CEOs are of great interest.

Macrocyclic polyester oligomers also can be prepared via the condensation of a dicarboxylic acid chloride with at least one bis(hydroxyalkyl) ester such as bis(4-hydroxybutyl) terephthalate in the presence of a highly unhindered amine or a mixture thereof with at least one other tertiary amine such as triethylamine. The condensation reaction is conducted in a substantially inert organic solvent such as methylene chloride, chlorobenzene, or a mixture thereof. See, for example, U.S. Pat. No. 5,231,161 to Brunelle et al.

These methods suffer from the relatively high cost of dicarboxylic acid chlorides and the need for a base to react with the hydrochloric acid formed in the process. These high manufacturing costs have in many cases prevented the use of macrocyclic ester oligomers commercially, and, therefore, lower cost routes to CEOs are of great interest.

Another method for preparing macrocyclic polyester oligomers or macrocyclic co-oligoesters is the depolymerization of linear polyester polymers in the presence of an organotin or titanate compound. In this method, linear polyesters are converted to macrocyclic polyester oligomers by heating a mixture of linear polyesters, an organic solvent, and a transesterification catalyst such as a tin or titanium compound. The solvents used, such as o-xylene and o-dichlorobenzene are usually substantially free of oxygen and water and solvents must be kept scrupulously dry when titanates are used as catalysts. See, for example, U.S. Pat. No. 5,407,984 to Brunelle et al. and U.S. Pat. No. 5,668,186 to Brunelle et al., and D. J. Brunelle in *Cyclic Polymers*, Second Edition, J. A. Semlyn (ed.), (2000), Kluwer Academic Publishers (Netherlands), pp. 185-228. The nature of ring-chain equilibrium dictates that the percent yield of cyclic versus linear species drops off significantly as the concentration of starting polymer increases.

More recently, it has been found that polyesters can be made from carboxylic diacids or their diesters and diols using enzymes that catalyze transesterification; see for instance X.Y. Wu, et al., *Journal of Industrial Microbiology and Biotechnology*, vol. 20, p. 328-332 (1998); E. M. Anderson, et al.; *Biocatalysis and Biotransformation*, vol. 16, p. 181-204 (1998); and H. G. Park, et al., *Biocatalysis*, vol. 11, p. 263-271 (1994). In some instances, in such reactions the production of small amounts of CEO coproducts has also been reported; see for instance G. Mezoul, et al., *Polymer Bulletin*, vol. 36, p. 541-548 (1996). There has also been a study reported on the amounts of CEOs that should be present in such reactions; see C. Berkane, et al., *Macromolecules*, vol. 30, p. 7729-7734 (1997). The latter study concluded that formation of the CEOs in the enzyme catalyzed reactions followed the same type of rules that govern the formations of these CEOs in nonenzymatic catalyzed reactions, and that only small fractions of CEOs should be produced in such enzymatic reactions unless they were done under very dilute conditions. In all of these references the byproduct alcohol or water from the transesterification/esterification was removed (usually by sparging with an inert gas) to drive the polymeric product to higher molecular weight.

A recent paper, A. Lavalette, et al., *Biomacromolecules*, vol. 3, p. 225-228 (2002), describes a process whereby an enzymatically catalyzed reaction of dimethyl terephthalate and di(ethylene glycol) or bis(2-hydroxyethyl)thioether leads to essentially complete formation of the dimeric cyclic ester, while use of 1,5-pentanediol leads to a relatively high yield of the dimeric cyclic ester, along with some linear polyester. The formation of high yields of the cyclic with di(ethylene glycol) and bis(2-hydroxyethyl)thioether is attributed to a π-stacking-type short range interaction which favored formation of the dimeric cyclic ester.

U.S. patent application publications 2004-0019177 and 2005-0054809 disclose enzyme-catalyzed processes for the preparation of polyester cyclic ester oligomers. Heretofore, however, it has been unknown in the art how to produce CEOs from the reaction of dicarboxylic acids and/or dicarboxylic acid derivatives with diols or from linear ester oligomers in mixtures of solvents that enhance the formation of the CEOs.

Surprisingly, it has been found that when dicarboxylic acids and/or dicarboxylic acid derivatives with diols or linear ester oligomers are reacted in the presence of an esterification/transesterification enzyme catalyst in an optimal mixture of reaction solvents a significantly increased yield of cyclic ester oligomer can be obtained.

SUMMARY OF THE INVENTION

There is disclosed and claimed herein a process for the production of cyclic ester oligomers, comprising the step of reacting in a solvent components comprising:

(a) a first component selected from one or more of:
  (i) at least one dicarboxylic acid and/or dicarboxylic acid derivative and at least one diol,
  (ii) at least one hydroxycarboxylic acid and/or hydroxycarboxylic acid ester, and
  (iii) at least one linear ester oligomer; and
(b) a second component comprising at least one enzyme capable of catalyzing transesterification of esters, esterification of carboxylic acids, and/or hydrolysis of esters;

wherein the solvent comprises about 30 to about 70 weight percent of at least one tertiary alcohol and about 30 to about 70 weight percent of at least one non-alcoholic solvent, wherein the weight percentages are based on the total weight of the solvent.

Further provided is a process for forming linear polyesters and molded linear polyester articles from the cyclic ester oligomers

DETAILED DESCRIPTION OF THE INVENTION

As used herein, the term "dicarboxylic acid" refers to an organic compound that has two carboxylic acid groups. The term "dicarboxylic acid derivative" refers to compounds derived from dicarboxylic acids such as a monoester, diester, or mixtures of two or more diesters, two or more monoesters, or at least one diester and at least one monoester. The dicarboxylic acid or dicarboxylic acid derivative may be substituted with one or more functional groups such as alkyl, halogen, ether, thioether, and oxo (keto) that do not substantially interfere with the various reactions described in the processes herein. The dicarboxylic acid or dicarboxylic acid derivative may include an aromatic ring as part of its structure. The dicarboxylic acid or dicarboxylic acid derivative may be an aliphatic dicarboxylic acid. The term "hydroxycarboxylic acid ester" means an organic compound that has a hydroxy group and a carboxylic acid ester group.

By a "diol" is meant an organic compound having 2 hydroxyl groups or a simple derivative thereof. The diol may be substituted with one or more functional groups such as halogen, ether, thioether, and oxo (keto) which do not substantially interfere with the various reactions described in the processes herein. The diol may include an aromatic ring as part of its structure.

By "monomer" is meant a dicarboxylic acid, dicarboxylic acid derivative, hydroxy carboxylic acid, hydroxy carboxylic acid ester, or diol, as defined above.

By a "cyclic ester oligomer" (CEO) is meant a cyclic compound that is derived from at least one dicarboxylic acid and/or dicarboxylic acid derivative and at least one diol, at least one hydroxycarboxylic acid and/or hydroxycarboxylic acid ester, or a combination of at least one dicarboxylic acid and/or dicarboxylic acid derivative, at least one diol, and at least one hydroxycarboxylic acid and/or hydroxycarboxylic acid ester. The moieties in the CEO derived from the diols, dicarboxylic acids and/or dicarboxylic acid derivatives, and hydroxycarboxylic acids and/or hydroxycarboxylic acid esters are connected by ester groups.

By a "dimeric" CEO herein is meant a cyclic compound derived from at least one dicarboxylic acid and/or dicarboxylic acid derivative and at least one diol that has two units derived from dicarboxylic acid and/or dicarboxylic acid derivative and two units derived from diols, while if the dimeric CEO is made from a hydroxycarboxylic acid and/or hydroxycarboxylic acid ester it is derived from two such molecules. Trimeric, tetrameric, etc. CEOs have analogous definitions. CEOs may be made from two or more different dicarboxylic acids and/or dicarboxylic acid derivatives, two or more different diols, and/or two or more hydroxycarboxylic acids and/or hydroxycarboxylic acid esters. CEOs will preferably have a degree of polymerization (DP) of about 1 to about 20, or preferably, about 1 to about 10, or more preferably, about 1 to about 5.

By a "linear ester oligomer" (LEO) herein is meant a linear compound derived from one or more dicarboxylic acids and/or dicarboxylic acid derivatives and one or more diols, one or more hydroxycarboxylic acids and/or hydroxycarboxylic acid esters, or a combination of one or more dicarboxylic acids and/or dicarboxylic acid derivatives, one or more diols, and one or more hydroxycarboxylic acids and/or hydroxycarboxylic acid esters is LEOs will preferably have a degree of polymerization (DP) of about 1 to about 20, or preferably, about 1 to about 10, or more preferably, about 1 to about 5.

LEOs may be made by melt polymerization; solution polymerization; enzyme-catalyzed polymerization; the depolymerization of polyesters, including the thermal depolymerization of polyesters and the alcoholysis (e.g. 20 methanolysis) and hydrolysis of polyesters; or other methods known to those skilled in the art. For examples of the use of melt polymerization, see F. W. Billmeyer, *Textbook of Polymer Science*, 3$^{rd}$ Edition (1984), John Wiley & Sons, pp. 25-48. For examples of the use of depolymerization, see Shibata, Mitsuhiro, et al., "Depolymerization of poly(butylenes terephthalate) using high-temperature and high-pressure methanol", *J. Applied Polymer Science*, (2000), 77(14), 3228-3233. For examples of the use of enzyme catalysis, see Kumar, Rajesh, et al., "Enzymatic Synthesis of multi-component copolymers and their structural characterization", *Polymer Preprints* (American Chemical Society, Division of Polymer Chemistry) (2003), 44(1), 998-999.

The term "linear ester oligomer" (LEO) also encompasses mixtures containing both at least one linear compound derived from one or more dicarboxylic acids and/or dicarboxylic acid derivatives and one or more diols, one or more hydroxycarboxylic acids and/or hydroxycarboxylic acid esters, or a combination of one or more dicarboxylic acids and/or dicarboxylic acid derivatives, one or more diols, and one or more hydroxycarboxylic acids and/or hydroxycarboxylic acid esters and CEOs that are naturally present when LEOs are formed by either polymerization or depolymerization in the presence of a transesterification catalyst. The amount of CEOs that will naturally be present is predicted by thermodynamic equilibrium, as taught by H. Jacobson and W. H. Stockmeyer in "Intermolecular Reaction and Polycondensation I. The Theory of Linear Systems", *The Journal of Chemical Physics*, Vol. 18 Number 12, December 1950.

One type of preferred diol that may be used in the process of the present invention or from which LEOs used in the process of the invention are derived is an aliphatic diol, that is a diol in which each hydroxyl group is bound to different alkyl carbon atoms. Other preferred diols include diols of the general formula $HOCH_2(CR^1R^2)_nCH_2OH$, wherein $R^1$ and $R^2$ are each independently hydrogen or an alkyl group and n is an integer of 0 to 10, and preferably all $R^1$ and $R^2$ are hydrogen and especially preferably n is 0 or an integer of 1 to 4, and more preferably is n is 1 or 2. Also preferred are diols of the general formula $HO((CH_2)_pO)_rH$, where p is 2-15 and r is 1-10. More preferred are diols of the same general formula where p is 2-10 and r is 1-5. Preferred diols include ethylene glycol, 1,3-propanediol, 1,4-butanediol, 1,5-pentanediol, 1,6-hexanediol, di(ethylene glycol), di(butylene glycol), di(propylene glycol), tri(butylene glycol), or mixtures thereof; dimethyl isophthalate with ethylene glycol, 1,3-propanediol, or 1,4-butanediol, 1,5-pentanediol, 1,6-hexanediol, di(ethylene glycol), di(butylene glycol), di(propylene glycol), tri(butylene glycol). Also preferred are alicyclic diols such as cyclohexane dimethanol. Aromatic diols such as hydroquinone may be used, as may thioethers.

Preferred dicarboxylic acids and/or dicarboxylic acid derivatives used in the process of the present invention or from which LEOs used in the invention are derived include aromatic dicarboxylic acids such as isophthalic acid, substituted isophthalic acids, terephthalic acid, substituted terephthalic acids, and 2,6-naphthalenedicarboxylic acid, and combinations thereof and their dicarboxylic acid derivatives. More preferred carboxylic acids are terephthalic acid and isophthalic acid and their dicarboxylic acid derivatives, and terephthalic acid and its dicarboxylic acid derivatives are especially preferred. Preferred aliphatic dicarboxylic acids and/or dicarboxylic acid derivatives are adipic acid, glutaric acid, succinic acid, sebacic acid, and maleic acid and their dicarboxylic acid derivatives. It is particularly preferred that a dicarboxylic acid derivative in the form of a diester be used. Any combination of preferred dicarboxylic acid and/or dicarboxylic acid derivatives and the diols specified in the general formula above may be used in the present invention.

Preferred combinations of dicarboxylic acids and/or dicarboxylic acid derivatives and diols used in the process of the present invention or from which LEOs used in the invention are derived include dimethyl terephthalate with ethylene glycol, 1,3-propanediol, 1,4-butanediol, 1,5-pentanediol, 1,6-hexanediol, di(ethylene glycol), di(butylene glycol), di(propylene glycol), tri(butylene glycol), or mixtures thereof; dimethyl isophthalate with ethylene glycol, 1,3-propanediol, or 1,4-butanediol, 1,5-pentanediol, 1,6-hexanediol, di(ethylene glycol), di(butylene glycol), di(propylene glycol), tri(butylene glycol), or mixtures thereof; dimethyl terephthalate with cyclohexane dimethanol; and dimethyl 2,6-naphthalenedicarboxylate with ethylene glycol, 1,3-propanediol, 1,4-butanediol, 1,5-pentanediol, 1,6-hexanediol, di(ethylene glycol), di(butylene glycol), di(propylene glycol), tri(butylene glycol), or mixtures thereof.

When used, hydroxycarboxylic acids and hydroxycarboxylic acid esters such as p-hydroxybenzoic acid and 2-hydroxyl-6-naphthoic acid and their esters will preferably be used as comonomers with diols and dicarboxylic acids and/or dicarboxylic acid derivatives.

In the process of the present invention, reactants are dissolved in a solvent and reacted in the presence of at least one enzyme to form cyclic ester oligomers. The reactants according to the present invention are one or more selected from the group consisting of at least one dicarboxylic acid and/or dicarboxylic acid derivative and at least one diol; at least one hydroxycarboxylic acid and/or at least one hydroxycarboxylic acid ester; and at least one linear ester oligomer.

The solvent used in the process of the present invention comprises about 30 to about 70 weight percent of at least one tertiary alcohol and about 30 to about 70 weight percent of at least on non-alcoholic solvent, or preferably about 40 to about 60 weight percent of at least one tertiary alcohol and about 40 to about 60 weight percent of at least on non-alcoholic solvent, based on the total weight of the solvent.

The tertiary alcohol solvent preferably has about 4 to about 8 carbon atoms and a general formula of $(R^1)(R^2)(R^3)COH$, where $R^1$, $R^2$, and $R^3$, are preferably independently selected from methyl, ethyl, n-propyl, i-propyl, n-butyl, iso-butyl, sec-butyl, tert-butyl, n-pentyl, 2-pentyl, 3-pentyl, and other pentyl isomers. Preferred tertiary alcohols are tert-amyl alcohol, 2,3-dimethyl-2-butanol, and 3-ethyl-3-pentanol.

The non-alcoholic solvent is any solvent that does not contain a hydroxy group and that is miscible with the tertiary alcohol and that will dissolve the reactants. Aromatic and/or chlorinated solvents are particularly suitable. Preferred non-alcoholic solvents include toluene, benzene, xylene, chlorobenzene, dichlorobenzene, methylene chloride, methyl tert-butyl ether, ethyl tert-butyl ether, methyl isobutyl ketone, and chloroform.

The enzyme used in the present invention is at least one enzyme that can catalyze the esterification of carboxylic acids, the transesterification of esters, and/or the hydrolysis of esters. Typical types of enzymes that may be used include lipases, proteases, and esterases. For example, see the chapter R. J. Kazlaukas, et al., "Biotransformation with Lipases," in *Biotechnology*, $2^{nd}$ Ed, Vol. 8a, Eds. H. J. Rehm et al., Wiley-VCH, Weinheim, Germany, p. 40-191 (1998). The enzyme is not soluble in the reaction mixture and may be attached to a solid material (supported or immobilized); see for instance G. E. Bickerstaff, Ed., *Immobilization of Enzymes and Cells*, Humana Press, Totowa, N.J., 1997. Supports may include materials such as diatomaceous earth, polysaccharides (e.g., chitosan, alginate or carrageenan), titania, silica, alumina, polyacrylates and polymethacrylates, and ion exchange resins, and the enzyme may be adsorbed, covalently attached, or ionically attached, or in the form of crosslinked enzyme crystals (CLECS). The enzyme may also be used without prior immobilization on a support and may be suspended in the stirred reaction mixture. The specific activity of the immobilized enzyme is preferably about 0.1 IU/g immobilized enzyme to about 2000 IU/g immobilized enzyme, more preferably about 10 IU/g immobilized enzyme to about 500 IU/g of immobilized enzyme.

Preferred enzymes for use in the present invention are bacterial and fungal enzyme catalysts that are derived from organisms of the genera *Aspergillus, Arthrobacter, Alcaligenes, Bacillus, Brevibacterium, Pseudomonas, Chromobacterium, Candida, Fusarium, Geotrichum, Humicola, Mucor, Pichia, Penicillium, Rhizomucor, Rhizopus* or *Thermus*. More preferred bacterial and fungal enzyme catalysts are derived from the genera and species *Arthrobacter* sp., *Alcaligenes* sp., *Aspergillus niger, Aspergillus oryzae, Bacillus cereus, Bacillus licheniformis, Bacillus subtilis, Bacillus coagulans, Brevibactedum ammoniagenes, Burkholderia plantaii, Candida antartica, Candida cylindracea, Candidia lipolytica, Candida utilis, Candida rugosa, Chromobactedium viscosum, Fusarium solani, Geotrichum candidum, Humicola lanuginosa, Mucor* sp., *Mucor japonicus, Mucor javanicum, Mucor miehei, Pichia miso, Rhizomucor miehei, Rhizopus* sp., *Rhizopus nigricans, Rhizopus oryzae, Rhizopus arrhizus, Rhizopus delemar, Rhizopus niveus, Penicillium acylase, Penicillium roqueforti, Thermus aquaticus, Thermus flavus, Thermus thermophilus, Chromobacterium viscosum, Burkholderia cepacia, Pseudomonas* sp., *Pseudomonas aeruginosa, Pseudomonas burkholderia, Pseudomonas cepacia, Pseudomonas fluorescens* or *Pseudomonas putida*. Particularly lipases are derived from *Burkholderia cepacia, Pseudomonas* sp, or *Candida antartica*, such as *Candida antartica* lipase B "CALB" (see Anderson et al., *Biocatalysis and Biotransformation*, 16:181-204 (1998)). Examples of suitable, commercially-available, catalysts derived from *C. antartica* include, but are not limited to, Novozym® 435 (Product# L4777, Sigma-Aldrich, Mo.) and CHIRAZYME L-2, c-f C2, lyo (ID# 2207257, BioCatalytics, Pasadena, Calif.). Preferred lipases derived from *Burkholderia cepacia* are PS-C "Amano" I and PS-D "Amano" I, available from Amano Enzyme, USA (Lombard, Ill.). Preferred lipases derived from *Pseudomonas* sp. are ICR-107, ICR-108, and ICR-113, available from BioCatalytics.

By the term "derived from" is meant that the enzyme can be isolated from or otherwise obtained from the specified organism. The enzyme may be used as part of a whole cell or a permeablized cell and may be partially purified or wholly purified.

The process of the present invention is run at temperatures at which the enzymes are active as catalysts for the desired reactions. The upper temperature limit is typically that at which the enzyme ceases to be an active catalyst. Often this is the temperature at which the enzyme is denatured in the reaction medium. This upper temperature will vary with the enzyme used and the process ingredients, especially the preselected solvent, used. Typically these temperatures may range from about 0° C. to about 130° C. (the latter using specialty enzymes for higher temperatures, such as enzymes isolated from thermophillic microorganisms). Higher temperatures (but below the temperature at which the enzyme ceases to be active) are usually preferred because reaction(s) are often faster and solubilities of the various process ingredients are usually higher at higher temperatures. In one embodiment of the invention, a preferred temperature range is between about 40 and about 100° C. and a more preferred temperature ranges is between about 60 and 80° C.

Preferred concentrations of the reactants in the process are at least 1 to about 25 w/v percent, more preferred concentrations are about 3 to about 15 w/v percent, based on the total weight of the reactants and the volume of the reaction mixture in g and mL, respectively. The upper limit for these concentrations may be dictated in part by the desire to retain the reactants in solution. These concentrations are at the temperature at which the reaction is run. The concentration may be allowed to vary during the reaction. Reactants can be added either continuously or at intervals throughout the reaction to maintain or alter the concentration.

When the reactants comprise dicarboxylic acid and/or dicarboxylic acid derivative and diol, the preferred ratio of dicarboxylic acid and/or dicarboxylic acid derivative to diol is between about 0.7:1 and 1.3:1.

The process of the present invention may be a batch, semi-batch, or continuous process. The enzyme may be attached to a solid support or used unsupported. It may be present as a fixed bed or may be suspended in the solvent.

Throughout the process, enough water must be present in the reaction mixture to keep the enzyme in a catalytically-active state. The reactants, if 10 not anhydrous, may provide the necessary concentration of water. A suitable amount of water may need to be added to the solvent at the beginning of the process, and it may be necessary to continue to add water throughout the process. The amount of water present throughout the reaction that is required to maintain the enzyme activity can be determined by measuring the rate of production of CEOs. For methods of assaying enzyme activity, see: J. Anderson, T. Byrne, K. J. Woelfel, J. E. Meany, G. T. Spyridis, Y. Pocker *Journal of Chemical Education*, vol. 71, 715-718 (1994); T. Furutani, R. Su, H. Ooshima, J. Kato *Enzyme and Microbial Technology*, vol. 17, 1067-1072 (1995); and J. Zhou, R. J. Ain, C. M. Riley, R. L. Schowen *Analytical Biochemistry*, vol. 231, 265-267 (1995). Generally, the more hydrophilic the solvent, the more water must be present, particularly if the reaction mixture continuously purged with an inert gas to remove byproducts of the transesterification/esterification process, such as any alcohols that are formed. For example, when hexane is used as the solvent, about 50 ppm of water may be required to maintain enzyme activity over the course of the reaction. When toluene is used, about 100 to about 200 ppm of water may be required to maintain enzyme activity over the course of the reaction and when methyl isobutyl ketone is used, about 400-500 ppm of water may be required. The water level present in the solvent can be determined using Karl-Fischer titration or other methods known to those skilled in the art.

The reaction mixture is preferably continuously purged during the process, preferably with an inert gas, to remove the byproducts of the transesterification/esterification process, such as any alcohols that are formed. The purging process may also remove water, requiring that water levels be maintained by the addition of water throughout the process in order to maintain enzyme activity. If the purging process removes solvent, additional solvent may have to be added throughout the process as well.

The CEOs formed by the process of the present invention may be recovered by any technique known in the art. For example, if the CEO is a solid, it may be recovered from solution by cooling the solution and/or removing some or all of the solvent and/or adding an additional solvent in which the CEO is not soluble, and recovering the solid CEO, for example, by filtration. The CEO may be recovered by crystallization, liquid-liquid extraction, or the like. Other techniques that could be used to isolate the CEOs from a mixture containing other components (such as starting materials or LEOs) include selective crystallization; passing a solution containing the CEO's through a semi-permeable membrane; using a distillation technique such as short-path distillation; sublimation, melt-crystallization; the use of a selective solvent or selective adsorbant, or the like.

Preferred CEOs formed by the process of this invention are the dimer derived from 1,4-butanediol and dimethyl terephthalate (3,8,15,20-tetraoxatricyclo[20.2.2.2$^{10,13}$]octacosa-10,12,22,24,25,27-hexaene-2,9,14,21-tetrone) (CBPT) (structure 1); the trimer formed from 1,4-butanediol and dimethyl terephthalate (3,8,15,20,27,32-hexaoxatetracyclo [32.2.2.2$^{10,13}$.2$^{22,25}$]dotetraconta-10,12,22,24,34,36,37, 39,41-nonaene-2,9,14,21,26,33-hexone); the dimer formed from 1,3-propanediol and dimethyl terephthalate (3,7,14,18-tetraoxatricyclo[18.2.2.2$^{9,12}$]hexacosa-9,11,20,22,23,25-hexaene-2,8,13,19-tetrone) (structure 2); the dimer formed from di(ethylene glycol) and dimethyl terephthalate (3,6,9, 16,19,22-hexaoxatricyclo[22.2.2.2$^{11,14}$]triaconta-11,13,24, 26,27,29-hexaene-2,10,15,23-tetrone) (structure 3); and the trimer formed from ethylene glycol and dimethyl terephthalate (3,6,13,16,23,26-hexaoxatetracyclo[26.2.2.2$^{8,11}$.2$^{18, 21}$]hexatriaconta -8,10,18,20,28,30,31,33,35-nonaene-2,7, 12,17,22,27-hexone).

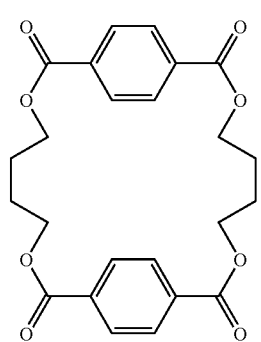

1

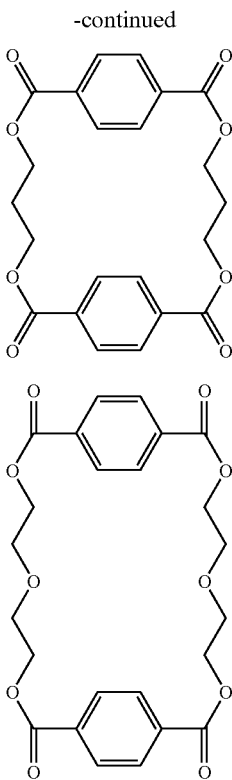

Also preferred CEOs are higher oligomers derived from 1,4-butanediol and dimethyl terephthalate, 1,3-propanediol and dimethyl terephthalate, di(ethylene glycol) and dimethyl terephthalate; oligomers derived from 1,4-cyclohexanedimethanol and dimethyl terephthalate; oligomers derived from 1,5-pentanediol and dimethyl terephthalate; oligomers derived from 1,6-hexanediol and dimethyl terephthalate; oligomers derived from ethylene glycol and dimethyl 2,6-naphthalenedicarboxylate; and CEOs derived from two or more of the above.

The CEOs formed by the process of the present invention may be polymerized to higher molecular weight linear polyesters, which have many applications in injection molding, blow molding, extrusion molding, fibers, filaments, and films and are useful for making durable and disposable goods.

The polymerization may occur in the process of forming the article, using processes such as, but not limited to, injection and rotational molding, resin film infusion, resin transfer molding, filament winding, powder coating to create a prepreg or film, hot melt prepreg preparation, compression molding, roll wrapping, and pultrusion. The polymerization preferably occurs at temperatures above the melting point of the CEOs.

The polymerization of CEO's to linear polyesters is described in U.S. Pat. Nos. 5,039,783, and 5,466,744 and reviewed by D. J. Brunelle in *Cyclic Polymers*, Second Edition, J. A. Semlyn (ed.), (2000), Kluwer Academic Publishers (Netherlands), pp. 185-228.

The polymerization is preferably done in the presence of a polymerization catalyst such as organotin compounds, titanate esters, carbenes, alkali metal salicylates, stannous alkoxides, organotin compounds, and metal acetylacetonates.

Additives such as reinforcing agents, mineral fillers, and other additives may be added to the CEO's before or during the polymerization to linear polyesters. The resulting polyesters will incorporate these additives. Examples of suitable additives can include glass fibers, fumed silica, titanium dioxide, calcium carbonate, chopped fibers, fly ash, glass microspheres, micro-balloons, crushed stone, nanoclay, linear polymers, boron nitride, colorants, pigments, magnetic materials, antioxidants, UV stabilizers, heat stabilizers, plasticizers, flame retardants, lubricants, and mold release agents.

The articles formed from the CEOs can include automotive body panels and chassis components, bumper beams, aircraft wing skins, windmill blades, fluid storage tanks, tractor fenders, tennis rackets, golf shafts, windsurfing masts, toys, rods, tubes, bars, stock, bicycle forks, and machine housings, and like.

EXAMPLES

Abbreviations

The following abbreviations are used: "DMT" means dimethyl terephthalate; "BDO" means 1,4-butanediol; "min" means minute(s); "g" means gram(s); "mg" means milligram(s); "mM" means millimolar; and "GC" means gas chromatography.

Materials

Dimethyl terephthalate (CAS# 120-61-6), and 1,4-butanediol (CAS# 110-63-4) were obtained from Aldrich Chemical Company (Milwaukee, Wisconsin) and were used as received. tert-Amyl alcohol (CAS# 75-85-4) was obtained from Aldrich Chemical Company (Milwaukee, Wis.). It was kept over activated 4Å molecular sieves before use and had a water content of about 380 ppm. Toluene (CAS# 109-88-3) was obtained from EMD Chemicals (Gibbstown, N.J.) and was kept as obtained over activated 4Å molecular sieves and had a water content of 130 ppm.

Product Analysis

The primary product of the reactions of Examples 1, 2, 5, and 6 and Comparative Examples 1-4, 7 and 12-15 was CPBT (Structure 1). Additional higher cyclic oligomers were also formed. The primary product of the reactions of Example 3 and Comparative Examples 8 and 9 is the dimeric CEO of 1,6-hexanediol and dimethyl terephthalate. Additional higher CEO's are also formed. The primary product of the reactions of Example 4 and Comparative Examples 10 and 11 is the dimeric CEO of 1,5-pentanediol and dimethyl terephthalate. Additional higher CEO's are also formed.

Samples are analyzed by LC using the following method. The reaction solvent used in the reaction mixture is stripped off under vacuum at a temperature of 30 to 50° C. Chloroform is added to about 1 to 3 times the original reaction volume before the solvent is removed. In some cases, the reaction solvent is not stripped off and the chloroform is added directly to the reaction mixture. Sufficient chloroform is added to dissolve the products and any remaining reactants. The amount of chloroform added depends on the original concentrations of reactants used. The unsupported or supported enzyme floats to the top of the chloroform while oligomers and unreacted diol and diester readily dissolve. An aliquot is removed from the clear solution and filtered. An equal volume of chloroform containing a suitable standard is added to the filtered aliquot and loaded into a LC vial. Analysis is carried out using a Waters-Alliance Separations HPLC 1100 module 2695 Liquid Chromatograph equipped with a UV diode array detector. A 250 mm by 4.6 mm, 5 micron particle size, Spherisorb silica column (cat. #Z226025, Supelco, Inc.) is utilized. A mixed mobile phase with a solvent gradient is used at a total flow rate of 0.5 ml/min. Initially a 50/50 by volume mixture of octane and chloroform is used for the mobile phase. This mixture changes linearly to 100% chloroform over 10 minutes and is then changed back to the 50/50 mixture at 25 minutes. Cyclic oligomer peaks are identified by retention time. Samples of pure cyclic oligomer extracted from the corresponding high molecular weight polymer or isolated from previous reactions are used to determine the retention times of the expected cyclic oligomer peaks. The identity of the peaks is independently confirmed by HPLC-MS. Concentrations of cyclic oligomers are determined using the internal standard and a response factor for the pure isolated oligomers relative to the standard. Apparent yields are based on the HPLC area percent of the cyclic components relative to the total area of all the peaks (other than the solvent and standard) observed in the HPLC.

Example 1 and Comparative Examples 1 and 2

A series of batch reactions were run in 40 mL glass vials reacting 1,4-butandiol (BDO) and dimethyl terephthalate (DMT) in the presence of the enzyme Novozym® 435. In the case of Example 1, the solvent used was a 50/50 by weight mixture of tert-amyl alcohol and toluene. In the case of Comparative Example 1, the solvent used was a 75/25 by weight mixture of tert-amyl alcohol and toluene. In the case of Comparative Example 2, the solvent used was toluene.

In each case, the BDO and DMT each had a nominal concentration of about 70 mM in the solvent. The nominal loading of the enzyme was 6 weight percent (which includes the enzyme support). The reactions were run in glass vials placed in a single, temperature-controlled heating block. Agitation was provided by magnetic stirring bars. The reactions were run for 96 hours at 70° C. The head spaces of the vials were swept with nitrogen saturated with the corresponding solvent mixture at the reaction temperature to remove the byproduct methanol. At the end of the reaction, the solvent was stripped off under vacuum at moderate temperature (about 50° C.), sufficient CHCl$_3$ to dissolve the reaction products and any unreacted starting material was added, and the mixture was agitated vigorously. The enzyme with support floated to the top. An aliquot of the resulting solution was taken for HPLC and GC analysis. HPLC analysis indicated >90% conversion based on the loss of DMT for all three reactions.

In the case of Example 1, the yield of cyclic oligomer was about 20%. In the case of Comparative Example 1, the yield of cyclic oligomer was about 7%. In the case of Comparative Example 2, the yield of cyclic oligomer was about 9%.

Example 2 and Comparative Examples 3 and 4

A series of batch reactions were run in 40 mL glass vials reacting 1,4-butandiol (BDO) and dimethyl terephthalate (DMT) in the presence of the enzyme Novozym® 435. In the case of Example 2, the solvent used was a 50/50 by weight mixture of tert-amyl alcohol and toluene. In the case of Comparative Example 3, the solvent used was a 75/25 by weight mixture of tert-amyl alcohol and toluene. In the case of Comparative Example 4, the solvent used was toluene.

In each case, the BDO and DMT each had a nominal concentration of about 75 mM. The nominal loading of the enzyme was 6 weight percent (which includes the enzyme support). The reactions were run in glass vials placed in a single, temperature-controlled heating block. Agitation was provided by magnetic stirring bars. The reactions were run for 168 hours at 70° C. The head spaces of the vials were swept with nitrogen saturated with the corresponding solvent mixture at the reaction temperature to remove the byproduct methanol. At the end of the reaction, the solvent was stripped off under vacuum at moderate temperature (about 50° C.), sufficient CHCl$_3$ to dissolve the reaction products and any unreacted starting material was added, and the mixture was agitated vigorously. The enzyme with support floated to the top. An aliquot of the resulting solution was taken for HPLC and GC analysis. HPLC analysis indicated >90% conversion based on the loss of DMT for all three reactions.

In the case of Example 2, the yield of cyclic oligomer was about 25%. In the case of Comparative Example 3, the yield of cyclic oligomer was about 3%. In the case of Comparative Example 4, the yield of cyclic oligomer was about 5%.

Comparative Examples 5-7

In the case of Comparative Examples 5-7, a non-enzymatic catalyst, the N-mesityl heterocyclic carbene-containing catalyst shown below was used for the (trans)esterification reaction.

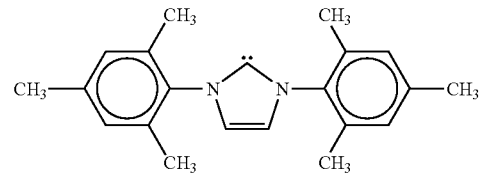

The batch reactions were done in 20 mL glass vials using a carefully controlled heated reaction block that was identical to that used in Examples 1 and 2 and Comparative Examples 1-4, as described above. In the case of Comparative Example 5, the solvent the solvent used was a 50/50 by weight mixture of tert-amyl alcohol and toluene. In the case of Comparative Example 6, the solvent used was a 75/25 by weight mixture of tert-amyl alcohol and toluene. In the case of Comparative Example 7, the solvent used was toluene.

In each case, the BDO and DMT each had a nominal concentration of about 70 mM in the solvent. The nominal loading of the mesityl heterocyclic carbene was 0.24 weight percent. The reactions were run in glass vials placed in a single, temperature-controlled heating block. Agitation was provided by magnetic stirring bars. The reactions were run for 8 hours at 50° C. The head spaces of the vials were swept with nitrogen saturated with the corresponding solvent mix at the reaction temperature to remove the by-product methanol. At the end of the reaction, the solvent was stripped off under vacuum at moderate temperature (about 50° C.), sufficient CHCl$_3$ to dissolve the reaction products and any unreacted starting material was added, and the mixture was agitated vigorously. An aliquot of the resulting solution was taken for HPLC and GC analysis. HPLC analysis indicated >90% conversion based on the loss of DMT for all three reactions.

In the cases of Comparative Examples 5 and 6, no formation of cyclic oligomer was observed. In the case of Comparative Example 7, the yield of cyclic ester oligomer was 6%.

Example 3 and Comparative Examples 8 and 9

A series of batch reactions between 1,6-hexanediol (HDO) and dimethyl terephthalate (DMT) is performed in 40-mL glass vials using a range of composition for reaction solvents, and using the enzyme Novozym® 435. In the case of Example 3, the solvent used is a 50/50 by weight mixture of tert-amyl alcohol and toluene. In the case of Comparative Example 8, the solvent used is a 75/25 by weight mixture of tert-amyl alcohol and toluene. In the case of Comparative Example 9, the solvent used is toluene.

In each case, the HDO and DMT each has a nominal concentration of about 70 mM in the solvent. The nominal loading of the immobilized enzyme is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates >90 % conversion of DMT and HDO for all three reactions. An improved yield of cyclic ester oligomers is observed in the case of Example 3 when compared to Comparative Examples 8 and 9.

Example 4 and Comparative Example 10 and 11

A series of batch reactions between 1,5-pentanediol (PDO) and dimethyl terephthalate (DMT) is performed in 40-mL glass vials using a range of composition for reaction solvents, and using the enzyme Novozym® 435. In the case of Example 4, the solvent used is a 50/50 by weight mixture of tert-amyl alcohol and toluene. In the case of Comparative Example 10, the solvent used is a 75/25 by weight mixture of tert-amyl alcohol and toluene. In the case of Comparative Example 11, the solvent used is toluene.

In each case, the PDO and DMT each has a nominal concentration of about 70 mM in the solvent. The nominal loading of the immobilized enzyme is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates >90 % conversion of DMT and HDO for all three reactions. An improved yield of cyclic ester oligomers is observed in the case of Example 4 when compared to Comparative Examples 10 and 11.

Example 5 and Comparative Example 12 and 13

A series of batch reactions between 1,4-butanediol (BDO) and dimethyl terephthalate (DMT) is performed in 40-mL glass vials using a range of composition for reaction solvents, and using the enzyme Novozym® 435. In the case of Example 5, the solvent used is a 50/50 by weight mixture of 2,3-dimethyl-2-butanol and toluene. In the case of Comparative Example 12, the solvent used is a 75/25 by weight mixture of 2,3-dimethyl-2-butanol and toluene. In the case of Comparative Example 13, the solvent used is toluene.

In each case, the BDO and DMT each has have a nominal concentration of about 70 mM in the solvent. The nominal loading of the immobilized enzyme is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates >90 % conversion of DMT and HDO for all three reactions. An improved yield of cyclic ester oligomers is observed in the case of Example 5 when compared to Comparative Examples 12 and 13.

Example 6 and Comparative Example 14 and 15

A series of batch reactions between 1,4-butanediol (BDO) and dimethyl terephthalate (DMT) is performed in 40-mL glass vials using a range of composition for reaction solvents, and using the enzyme Novozym® 435. In the case of Example 5, the solvent used is a 50/50 by weight mixture of 3-ethyl-3-pentanol and toluene. In the case of Comparative Example 14, the solvent used is a 75/25 by weight mixture of 3-ethyl-3-pentanol and toluene. In the case of Comparative Example 15, the solvent used is toluene.

In each case, the BDO and DMT each has a nominal concentration of about 70 mM in the solvent. The nominal loading of the immobilized enzyme is 6 weight percent. The reactions were run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates >90 % conversion of DMT and HDO for all three reactions. An improved yield of cyclic ester oligomers is observed in the case of Example 6 when compared to Comparative Examples 14 and 15.

Comparative Example 16

A 200 mg sample of each of the enzymes in Table 1 was added to its own 8 mL reaction vial equipped with a magnetic stirring bar. DMT (97 mg), DEG (500 µL of a solution prepared by dissolving 530 mg of DEG in 5 mL of toluene), and 1.4 mL of toluene were added to each vial. The resulting concentration of DEG was about 0.25 M. The vials were incubated at 50° C. with stirring for 96 hours under a flow of nitrogen saturated with toluene. The reactions were stopped by removal of toluene under vacuum, a sufficient volume of chloroform was added to dissolve all products and unreacted starting materials, and the resulting mixture was filtered to remove the undissolved enzyme using a 60 µm-porosity glass filter. The filtrates were analyzed by gas chromatography for DMT conversion, and by HPLC for cyclic ester oligomer (CEO) concentration. The results are shown in Table 1.

A reaction performed in exactly the same way but without any enzyme present was run as a control. No significant conversion of DMT or production of CEO was observed.

TABLE 1

| Enzyme | Enzyme source | Enzyme supplier | DMT conversion (%) | CEO (mM) |
|---|---|---|---|---|
| Novozym ® 435 | Candida antarctica | Novozymes | 100 | 120 |
| PS-C "Amano" I | Burkholderia cepacia | Amano | 100 | 1.6 |
| PS-D "Amano" I | Burkholderia cepacia | Amano | 38 | 0.4 |
| ICR-107 | Pseudomonas sp. | BioCatalytics | 19 | 1.5 |
| ICR-108 | Pseudomonas sp. | BioCatalytics | 12 | 0.1 |
| ICR-113 | Pseudomonas sp. | BioCatalytics | 92 | 7.0 |

Example 7 and Comparative Examples 17 and 18

A series of batch reactions between 1,6-hexanediol (HDO) and dimethyl terephthalate (DMT) is performed in 40-mL glass vials, where each reaction uses specified reaction solvent and one of the following enzymes (see Table 1): PS-C "Amano" I, PS-D "Amano" I, ICR-107, ICR-108, ICR-113. In the case of Example 7, the solvent used is a 50/50 by weight mixture of tert-amyl alcohol and toluene. In the case of Comparative Example 17, the solvent used is a 75/25 by weight mixture of tert-amyl alcohol and toluene. In the case of Comparative Example 18, the solvent used is toluene. A total of 15 reactions are run.

In each case, the HDO and DMT each has a nominal concentration of about 70 mM in the solvent. The nominal loading of the immobilized enzyme is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates at least about 10% conversion of DMT and HDO for each of the reactions. An improved yield of cyclic ester oligomers is observed in the case of Example 7 when compared to Comparative Examples 17 and 18.

Example 8 and Comparative Example 19 and 20

A series of batch reactions between 1,5-pentanediol (PDO) and dimethyl terephthalate (DMT) is performed in 40-mL glass vials where each reaction uses specified reaction solvent and one of the following enzymes (see Table 1): PS-C "Amano" I, PS-D "Amano" I, ICR-107, ICR-108, ICR-113. In the case of Example 8, the solvent used is a 50/50 by weight mixture of tert-amyl alcohol and toluene. In the case of Comparative Example 19, the solvent used is a 75/25 by weight mixture of tert-amyl alcohol and toluene. In the case of Comparative Example 20, the solvent used is toluene. A total of 15 reactions are run.

In each case, the PDO and DMT each has a nominal concentration of about 70 mM in the solvent. The nominal loading of the immobilized enzyme A is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates at least about 10% conversion of DMT and HDO for each of the reactions. An improved yield of cyclic ester oligomers is observed in the case of Example 8 when compared to Comparative Examples 19 and 20.

Example 9 and Comparative Example 21 and 22

A series of batch reactions between 1,4-butanediol (BDO) and dimethyl terephthalate (DMT) is performed in 40-mL glass vials where each reaction uses specified reaction solvent and one of the following enzymes (see Table 1): PS-C "Amano" I, PS-D "Amano" I, ICR-107, ICR-108, ICR-113. In the case of Example 9, the solvent used is a 50/50 by weight mixture of 2,3-dimethyl-2-butanol and toluene. In the case of Comparative Example 21, the solvent used is a 75/25 by weight mixture of 2,3-dimethyl-2-butanol and toluene. In the case of Comparative Example 22, the solvent used is toluene. A total of 15 reactions are run.

In each case, the BDO and DMT each has have a nominal concentration of about 70 mM in the solvent. The nominal loading of the immobilized enzyme is 6 weight percent. The reactions are run in glass vials placed in a single, temperature-controlled heating block. Agitation is provided by magnetic stirring bars. The reactions are run for 96 h at 70° C. The head spaces of the vials are swept with nitrogen saturated with the corresponding 5 solvent mixture at the reaction temperature to remove the by-product methanol. At the completion of the reaction, the solvent is stripped off under vacuum at moderate temperature (about 50° C.), sufficient $CHCl_3$ to dissolve the reaction products and any unreacted starting material is added, and the mixture is agitated vigorously. The immobilized enzyme is separated from the 1o mixture, and a sample of the resulting solution is analyzed by HPLC and GC.

HPLC analysis indicates at, least about 10% conversion of DMT and HDO for each of the reactions. An improved yield of cyclic ester oligomers is observed in the case of Example 9 when compared to Comparative Examples 21 and 22.

Example 10 and Comparative Example 23 and 24

A series of batch reactions between 1,4-butanediol (BDO) and dimethyl terephthalate (DMT) is performed in 40-mL glass vials where each reaction uses specified reaction solvent and one of the following enzymes (see Table 1): PS-C "Amano" I, PS-D "Amano" I, ICR-107, ICR-108, ICR-113. In the case of Example 10, the solvent used is a 50/50 by weight mixture of 3-ethyl-3-pentanol and toluene. In the case of Comparative Example 23, the solvent used is a 75/25 by weight mixture of 3-ethyl-3-pentanol and toluene. In the case of Comparative Example 24, the solvent used is toluene. A total of 15 reactions are run.

In each case, the BDO and DMT each has a nominal concentration of about 70 mM in the solvent. The nominal loading of the immobilized enzyme is 6 weight percent. The reactions were run in glass vials placed in a single, temperature-controlled heating block. Agitation is provided by magnetic 30 stirring bars. The reactions are run for 96 h at 70° C. The head spaces of the vials are swept with nitrogen saturated with the corresponding solvent mixture at the reaction temperature to remove the by-product methanol. At the completion of the reaction, the solvent is stripped off under vacuum at moderate temperature (about 50 °C.), sufficient $CHCl_3$ to dissolve the reaction products and any unreacted starting material is added, and the mixture is agitated vigorously. The immobilized enzyme is separated from the mixture, and a sample of the resulting solution is analyzed by HPLC and GC. HPLC analysis indicates at least about 10 % conversion of DMT and HDO for each of the reactions. An improved yield of cyclic ester oligomers is observed in the case of Example 10 when compared to Comparative Examples 23 and 24.

What is claimed is:

1. A process for the production of cyclic ester oligomers, comprising the step of reacting in a solvent components comprising:
   (a) a first component selected from one or more of:
      (i) at least one dicarboxylic acid and/or dicarboxylic acid derivative and at least one diol,
      (ii) at least one hydroxycarboxylic acid and/or hydroxycarboxylic acid ester, and
      (iii) at least one linear ester oligomer; and
   (b) a second component comprising at least one enzyme capable of catalyzing transesterification of esters, esterification of carboxylic acids, and/or hydrolysis of esters;
   wherein the solvent comprises about 30 to about 70 weight percent of at least one tertiary alcohol and about 30 to about 70 weight percent of at least one non-alcoholic solvent, wherein the weight percentages are based on the total weight of the solvent.

2. The process of claim 1, wherein the tertiary alcohol has about 4 to about 8 carbon atoms and a general formula of $(R^1)(R^2)(R^3)COH$, where $R^1$, $R^2$, and $R^3$, are independently selected from methyl, ethyl, n-propyl, i-propyl, n-butyl, isobutyl, sec-butyl, tert-butyl, n-pentyl, 2-pentyl, and 3-pentyl.

3. The process of claim 2, wherein the tertiary alcohol is tert-amyl alcohol.

4. The process of claim 2, wherein the tertiary alcohol is 2,3-dimethyl-2-butanol or 3-ethyl-3-pentanol.

5. The process of claim 1, wherein the non-alcoholic solvent is at least one selected from toluene, benzene, xylene, chlorobenzene, dichlorobenzene, methylene chloride, methyl tert-butyl ether, methyl isobutyl ketone, and chloroform.

6. The process of claim 5, wherein the non-alcohol solvent is toluene.

7. The process of claim 1, wherein component (a) comprises at least one diol of the formula $HO((CH_2)_pO)_rH$, where p is 2-15 and r is 1-10, and dimethyl terephthalate.

8. The process of claim 1, wherein component (a) comprises at least one diol of the formula $HO((CH_2)_pO)_rH$, where p is 2-10 and r is 1-5, and dimethyl terephthalate.

9. The process of claim 1, wherein component (a) comprises one or more diols selected from ethylene glycol, 1,3-propanediol, 1,4-butanediol, 1,5-pentanediol, 1,6-hexanediol, di(ethylene glycol), di(butylene glycol), di(propylene glycol), cyclohexane dimethanol and tri(butylene glycol) and one or more of dimethyl terephthalate, dimethyl isophthalate, and dimethyl 2,6-naphthalenedicarboxylate.

10. The process of claim 1, wherein component (a) comprises at least one linear ester oligomer derived from diols of the formula $HO((CH_2)_pO)_rH$, where p is 2-15 and r is 1-10, and dimethyl terephthalate.

11. The process of claim 1, wherein component (a) comprises at least one linear ester oligomer derived from one or more diols selected from ethylene glycol, 1,3-propanediol, 1,4-butanediol, 1,5-pentanediol, 1,6-hexanediol, di(ethylene glycol), di(butylene glycol), di(propylene glycol), cyclohexane dimethanol and tri(butylene glycol) and one or more of dimethyl terephthalate, dimethyl isophthalate, and dimethyl 2,6-naphthalenedicarboxylate.

12. The process of claim 1, wherein the enzyme is supported.

13. The process of claim 1, wherein the enzyme is unsupported.

14. The process of claim 12, wherein the enzyme is supported by materials selected from the group consisting of diatomaceous earth, polysaccharides, including chitosan, alginate or carrageenan, titania, silica, alumina, polyacrylates and polymethacrylates.

15. The process of claim 1, wherein the enzyme is a lipase, protease, or esterase.

16. The process of claim 15, wherein the enzyme is a lipase.

17. The process of claim 16, wherein the lipase is derived from *Candida antartica, Burkholderia cepacia*, or *Pseudomonas* sp.

18. The process of claim 17, wherein the lipase derived from *Candida antartica* is *Candida antartica* lipase B.

19. A process for the production of a linear polyester, comprising the steps of forming cyclic ester oligomers by reacting in a solvent components comprising:
   (a) a first component selected from one or more of:
      (i) at least one dicarboxylic acid and/or dicarboxylic acid derivative and at least one diol,
      (ii) at least one hydroxycarboxylic acid and/or hydroxycarboxylic acid ester, and
      (iii) at least one linear ester oligomer; and
   (b) a second component comprising at least one enzyme capable of catalyzing transesterification of esters, esterification of carboxylic acids, and/or hydrolysis of esters;
   wherein the solvent comprises about 30 to about 70 weight percent of at least one tertiary alcohol and about 30 to about 70 weight percent of at least one non-alcoholic solvent, wherein the weight percentages are based on the total weight of the solvent;
   and polymerizing the resulting cyclic ester oligomers to form a linear polyester.

20. A process for forming a molded linear polyester article, comprising the steps of forming cyclic ester oligomers by reacting in a solvent components comprising:
   (a) a first component selected from one or more of:
      (i) at least one dicarboxylic acid and/or dicarboxylic acid derivative and at least one diol,
      (ii) at least one hydroxycarboxylic acid and/or hydroxycarboxylic acid ester, and
      (iii) at least one linear ester oligomer; and
   (b) a second component comprising at least one enzyme capable of catalyzing transesterification of esters, esterification of carboxylic acids, and/or hydrolysis of esters;
   wherein the solvent comprises about 30 to about 70 weight percent of at least one tertiary alcohol and about 30 to about 70 weight percent of at least one non-alcoholic solvent, wherein the weight percentages are based on the total weight of the solvent;

a placing the resulting cyclic ester oligomers into a mold, polymerizing the cyclic ester oligomers to form a linear polyester article, and removing the article from the mold.

21. The process of claim 20, wherein the cyclic ester oligomers are placed in the mold in the presence of a polymerization catalyst.

22. The process of claim 20, wherein the cyclic ester oligomers are placed in the mold in the presence of a polymerization catalyst and at least one additive.

23. A linear polyester article made by the process of claim 20.

24. The article of claim 23 in the form of an automotive body panel or chassis component, bumper beam, aircraft wing skin, windmill blade, fluid storage tank, tractor fender, tennis racket, golf shaft, windsurfing mast, toy, rod, tube, bar, stock, bicycle fork, and machine housing.

* * * * *